(12) United States Patent
Xu et al.

(10) Patent No.: US 9,457,198 B2
(45) Date of Patent: Oct. 4, 2016

(54) ULTRA-LOW FREQUENCY MAGNETIC STIMULATING DEVICE AND OPERATIONAL METHOD THEREOF

(75) Inventors: Jianlan Xu, Beijing (CN); Enping Liu, Shenzhen (CN); Jiankai Hou, Shenzhen (CN); Hinghoi Hau, Shenzhen (CN)

(73) Assignee: Shenzhen Cornley Hi-Tech Co., Ltd., Shenzhen, Guangdong (CN)

( * ) Notice: Subject to any disclaimer, the term of this patent is extended or adjusted under 35 U.S.C. 154(b) by 160 days.

(21) Appl. No.: 13/201,787

(22) PCT Filed: Feb. 18, 2009

(86) PCT No.: PCT/CN2009/000162
§ 371 (c)(1),
(2), (4) Date: Aug. 16, 2011

(87) PCT Pub. No.: WO2010/094147
PCT Pub. Date: Aug. 26, 2010

(65) Prior Publication Data
US 2011/0301402 A1 Dec. 8, 2011

(51) Int. Cl.
*A61N 2/00* (2006.01)
*A61N 1/32* (2006.01)
(Continued)

(52) U.S. Cl.
CPC ............ *A61N 2/006* (2013.01); *A61N 1/32* (2013.01); *A61N 1/40* (2013.01); *A61N 2/02* (2013.01)

(58) Field of Classification Search
CPC ........ A61N 2/006; A61N 2/02; A61N 2/008; A61N 1/0484; A61N 1/36025; A61N 1/32; A61N 1/36071; A61N 1/36082; A61B 5/6803
USPC ............................................ 600/9–15; 607/2
See application file for complete search history.

(56) References Cited

U.S. PATENT DOCUMENTS 3,890,953 A * 6/1975 Kraus et al. .................... 600/14
5,527,259 A 6/1996 Grace et al.
(Continued)

FOREIGN PATENT DOCUMENTS

CN 87213121 U 3/1988
CN 1067588 A 1/1993
(Continued)

OTHER PUBLICATIONS

International Search Report for International Application No. PCT/CN2009/00162, mailed Dec. 3, 2009, 4 pages.
(Continued)

*Primary Examiner* — Christine H Matthews
*Assistant Examiner* — Kaylee Wilson
(74) *Attorney, Agent, or Firm* — Finnegan, Henderson, Farabow, Garrett & Dunner, LLP

(57) ABSTRACT

An ultra-low frequency magnetic stimulating device comprises a control module for generating a stimulating signal with a frequency lower than 20 Hz, an electric level shifting and converting circuit for shifting the electric level of the stimulating signal to form an AC stimulating signal, and an output module for power amplifying the AC stimulating signal and generating an electric current, an electric field or a magnetic field. The output of the ultra-low frequency magnetic stimulating device is a non-pulsed ultra-low frequency (lower than 20 Hz) current, an electric field or a magnetic field. The output current can be used for electrotherapy when being output to an electrode, or for magnetotherapy when being output to a coil, so as to cure or release diseases related to human brains.

10 Claims, 5 Drawing Sheets

(51) Int. Cl.
*A61N 1/40* (2006.01)
*A61N 2/02* (2006.01)

(56) References Cited

U.S. PATENT DOCUMENTS

| | | | | |
|---|---|---|---|---|
| 6,004,257 | A | * 12/1999 | Jacobson | A61N 2/02 600/9 |
| 6,561,968 | B1 | * 5/2003 | Dissing et al. | 600/13 |
| 2002/0165583 | A1 | * 11/2002 | Tepper et al. | 607/2 |
| 2003/0028072 | A1 | * 2/2003 | Fischell et al. | 600/13 |

FOREIGN PATENT DOCUMENTS

| CN | 1083403 A | 3/1994 |
|---|---|---|
| CN | 1086445 A | 5/1994 |
| CN | 1393270 A | 1/2003 |
| CN | 1879906 A | 12/2006 |
| WO | WO 99/06106 A1 | 2/1999 |

OTHER PUBLICATIONS

STMicroelectronics, TDA7294, 100V-100W DMOs Audio Amplifier With Mute/ST-BY, Apr. 2003, 17 pages.
Phillips Semiconductors, UDA134ITS Economy audio CODEC for MiniDisc (MD) home stero and portable applications, Product Specification, May 16, 2002, 36 pages.

\* cited by examiner

ULTRA-LOW FREQUENCY MAGNETIC STIMULATING DEVICE AND OPERATIONAL METHOD THEREOF

FIELD OF THE INVENTION

The invention relates to medical devices, particularly to an ultra-low frequency stimulating device and its operational method.

BACKGROUND OF THE INVENTION

Modern medical researches have shown that the human cerebral tissues including the cerebrum and the cerebellum are very sensitive to magnetic signals. Magnetic stimulus can improve the local blood circulation of the cerebrum, stipulate the restoration of cerebral cells, and activate the cerebral tissues. Utilizing the brain sensitivity to a magnetic field, magnetic induction can be carried out to the brain to cure and prevent neurological diseases without trauma but with high safety for using magnetic stimulus. Currently, the magnetic field for magnetic stimulus is a pulsed magnetic field with relatively high frequency, which is used mainly for diagnosis of neurological diseases and hardly has satisfactory effect of treating the diseases. Meanwhile, scientific research has also found that magnetic stimuli with different frequency bands have different biological effects on the brain.

The prior art of the technique has no medical devices which have the function of regulating the brain neurotransmitter by generating a current with an ultra-low frequency to act on a brain through electrodes or coils and then regulating the brain function. However, with the increasing pressure caused by social competition, psychic and psychological diseases have become a challenge to the human beings. It is therefore very necessary to regulate the cerebral functions for modern human beings.

SUMMARY OF THE INVENTION

To overcome at least one of the above-mention problems, this invention provides an ultra-low frequency magnetic stimulating device for curing and remitting diseases related to the brain, as well as an operational method for said device.

According to the invention, an ultra-low frequency magnetic stimulating device is provided, which comprises a control module, an electric level shifting and converting circuit, an output module, wherein, The control module is for generating a DC stimulating signal with a frequency lower than 20 Hz;

The electric level shifting and converting circuit is for shifting the electric level of said stimulating signal to form an AC stimulating signal;

The output module is for power-amplifying of the AC stimulating signal and generating an electric current, an electric field or a magnetic field.

The control module includes an ARM processor and an audio chip wherein said audio chip generates said DC stimulating signal under the control of said ARM processor.

The device further comprises a man-machine interface communicated with the ARM processor to achieve a man-machine interface control.

The control module is formed by a development board of the type of QQ2440V3. The audio chip is UDA1341TS, which is short-circuited through a capacitor (C46) and a capacitor (C45) at the audio chip's output terminals, and is grounded through a resistor (R9) and a resistor (R4) at the audio chip's output terminals.

The output module includes at least one power amplifying circuit, whose output terminal is connected with a coil.

The output module includes at least one power amplifying circuit, whose output terminal is connected with an electrode.

Said AC stimulating signal is a 0V-referenced AC stimulating signal.

Said power amplifying circuit is the TDA7249 chip. Said control module is further used for generating a mute control signal for the TDA7249 chip.

The control module is the ARM processor. The electric level shifting and converting circuit is further used for the voltage conversion of the mute control signal to convert the mute control signal with a high level of 3.3V into a mute control signal with a high level of 5V and outputting the latter to the TDA7249 chip.

The output current is a non-pulsed ultra-low frequency current with mono-frequency and/or a combination of non-pulsed ultra-low frequency currents with multi-frequency. The mono-frequency current and/or multi-frequency combined current are output simultaneously or in a time-sharing way.

The multi-frequency combined current is output in a modulated mode or in a superposed mode.

The invention further provides an operational method for an ultra-low frequency magnetic stimulating device, comprising:

Step 1, generating a DC stimulating signal with a frequency lower than 20 Hz;

Step 2, shifting the level of stimulating signal to form an AC stimulating signal;

Step 3, power-amplifying the AC stimulating signal and generating an electric current, an electric field or a magnetic field.

DETAILED DESCRIPTION OF THE PREFERRED EMBODIMENT

Figure 1:
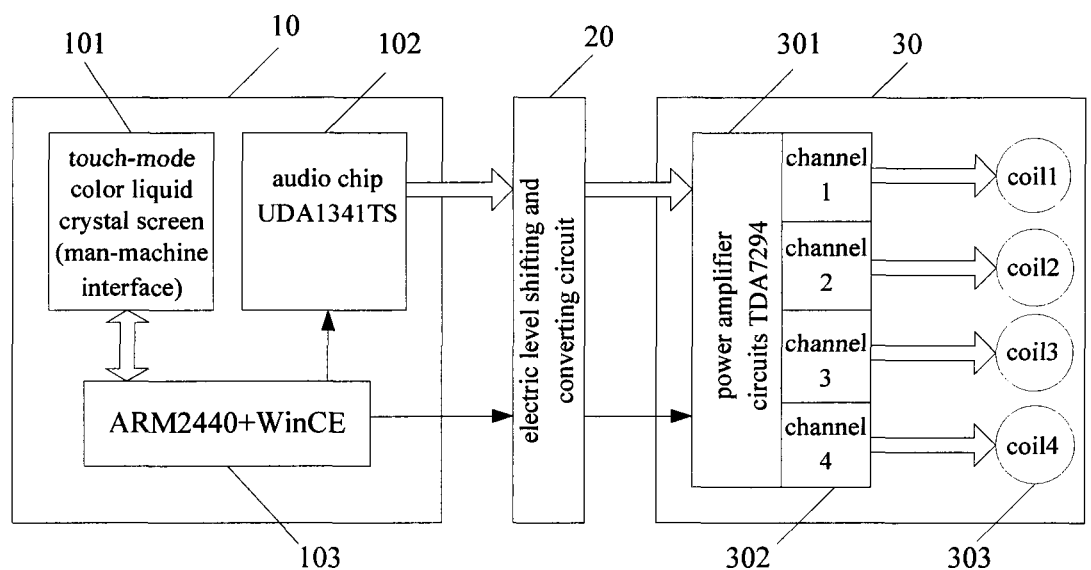
FIG. 1 shows the schematic diagram of the electric circuit of the ultra-low frequency magnetic stimulating device according to the invention.

As shown in FIG. 1, the ultra-low frequency magnetic stimulating device according to the invention comprises a control module 10, an electric level shifting and converting circuit 20 and an output module 30. The control module 10 comprises an ARM processor 103, a touch-mode color liquid crystal screen 101, and an audio chip 102. The output module 30 can comprise four power amplifier circuits 301 and correspondingly four coils 303, although the number of the power amplifier(s) can be set by the manufacturer, wherein each power amplifier circuit 301 has a channel 302. The ARM processor 103 is connected to the touch-mode color liquid crystal screen 101. While the ARM processor 103 is directly connected with the electric level shifting and converting circuit 20 at the ARM processor's output terminal(s), it is also connected to the electric level shifting and converting circuit 20 through the audio chip 102. The electric level shifting and converting circuit 20 is connected with the power amplifying circuits 301 through the in-parallel ultra-low frequency signal output lines and the mute control lines. Each terminal of the four power amplifiers 301 is respectively connected to one coil 303 with a stimulating frequency 0.001 Hz~20 Hz. The terminal of the power amplifier circuit can be alternatively connected to an electrotherapeutical electrode (not shown) with an electrotherapeutical frequency 0.001 Hz~20 Hz.

The output from the device can be a non-pulsed ultra-low frequency current, electric field or magnetic field of a frequency lower than 20 Hz, preferably 0.2 Hz. The output current can be output to the electrode for electro-therapy or to the coil 303 for magnetic-therapy. However, each output terminal can be only connected with either the electrode or the coil. The output current can be a non-pulsed ultra-low frequency current with mono-frequency and a combination of non-pulsed ultra-low frequency currents with multi-frequency, wherein the mono-frequency current and the multi-frequency combined current can be output simultaneously or in a time-sharing way. Alternatively, the output current can be a combination of the currents with multiple frequencies, which can be output in a modulated mode or in a superposed mode. The stimulating frequency is continuously adjustable with a step of 0.001 Hz over the range of 0.001 Hz-20 Hz for regulation. The maximum magnetic strength can be 200 Gauss, which is also continuously adjustable. The waveform output can be in the form of single sinusoidal wave or the superposition of multiple sinusoidal waves.

The hardware of the ultra-low frequency magnetic stimulating device is composed of three parts, which are the ARM processor (containing an operational system) 103, the electric level shifting and converting circuit 20, and the output module 30. The ARM processor 103 is used for controlling a man-machine interaction interface, generating ultra-low stimulating signals, the mute control, setting and storing treatment schemes, and the magnetic field calibration, etc. The electric level shifting and converting circuit 20 is used for shifting the potentials of the output signals from the ARM into 0V-referenced ultra-low signals and outputting the latter to the power amplifier circuits, and for converting the levels of the mute signals from the ARM to satisfy the control requirement of the subsequent power amplifier circuits. The output module 30 is used for amplifying the power of the ultra-low frequency stimulating signals and outputting said signals through the coils to generate an alternating ultra-low frequency stimulating magnetic field. The device of the invention can be powered through a transformer with a power of 1500 W, a primary input of 220 VAC, and a secondary output including two channels of 28 VAC and two channels of 12 VAC, wherein two channels of 28V outputs are used for providing power supply for the power amplifier circuit board after being series-connected and rectified while two channels of 12V outputs are used for providing power supply for the electric level shifting and converting circuit and the ARM control module after being series-connected and rectified. Said device can apply magnetic conduction to the human brain through ultra-low frequency continuous magnetic field to realize a cure and release of the mental diseases.

Preferably, said control module can be formed by a developing board of the type QQ2440V3 produced by Guangzhou Youshanzhibi Company, whose audio chip UDA1341TS can be short-circuited through two capacitors C45 and C46 at its output terminals while the resistors R4 and R9 are grounded to remove the filtering function. The QQ2440V3 developing board can be used as the master control board of the control module. The liquid crystal displayer can be formed by a 7 inches colorful liquid crystal screen that matches the developing board. Changes can be made to the ARM developing board depending on requirement, i.e. the capacitors C45 and C46 at the output terminals of the UDA1341TS audio chip can be short-circuited while the resistors R4 and R9 can be removed. It is because that in this invention the audio chip is used for outputting ultra-low frequency stimulating signals, while the audio output with the frequency lower than 10 Hz will be filtered according to the design of the original developing board. Therefore, the filter components are removed in this invention to generate ultra-low frequency signals.

According to the particular application of the device, a special WinCE5.0 inner kernel can be customized, which can load automatically the user's program on a SD card when the system starts.

Furthermore, an application program for the ultra-low frequency magnetic stimulating system is designed, which can realize the functions of convenient setting of waveform parameters, magnetic field calibration, setting and storage of eight stimulus projects, stimulus timing, and on-line strength adjustment, etc.

Figure 2:
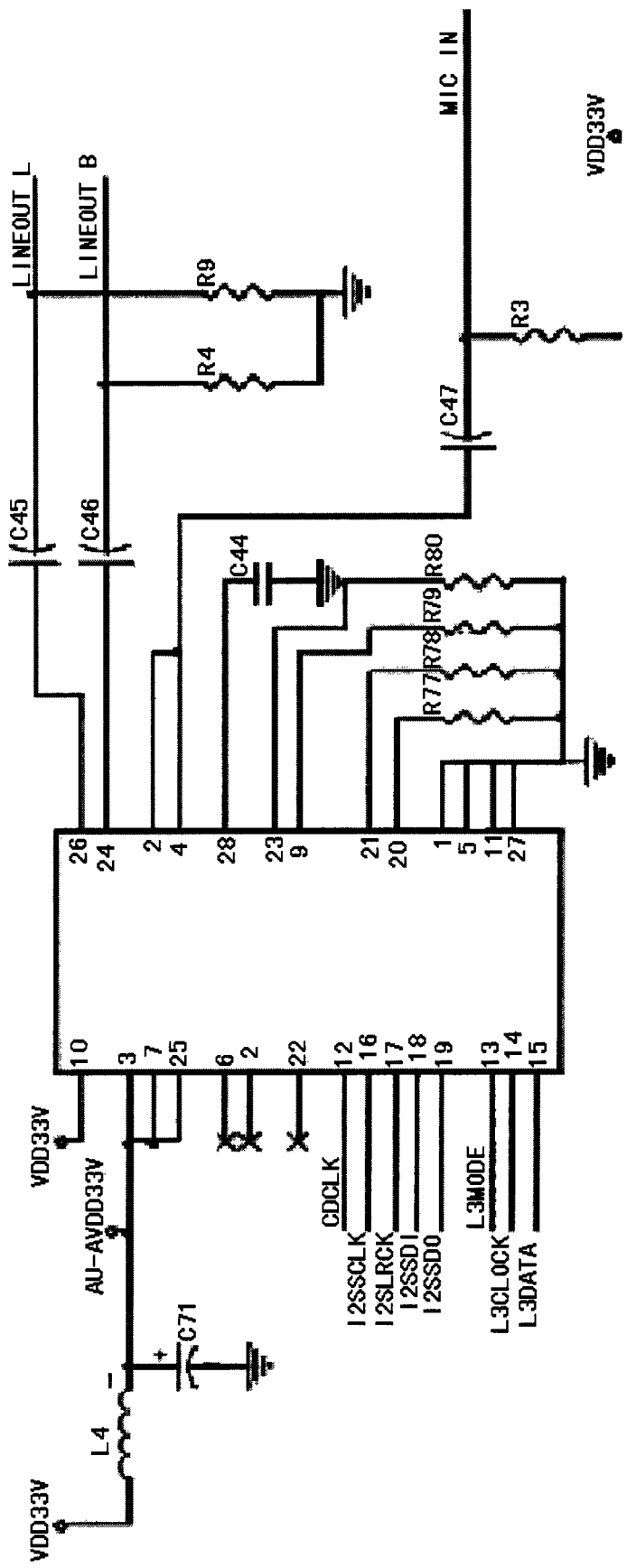
FIG. 2 shows the schematic diagram of the audio output circuit of the ultra-low frequency magnetic stimulating device according to the invention.

Preferably, as shown in FIG. 2, pins 1, 5, 11 and 27 of the audio chip UDA1341TS are grounded directly. Pins 23, 9, 21, 20 are grounded through 10KΩ resistors R77, R78, R79, R80 respectively. Pin 28 is grounded through a 0.1 μF capacitor C44. Pins 2, 4 are connected with each other and then connected with the MIC IN and a 47KΩ resistor R3 in-parallel through a capacitor C47, wherein R3 is connected with the VDD33V through a 100KΩ resistor R11 and grounded through said resistor R11 and a 10 μF capacitor C48. Pin 26 is connected with LINEOUT L through a 10 μF capacitor C45 and grounded through said capacitor C45 and a 10KΩ resistor R9. Pin 24 is connected with LINEOUT B through a 10 μF capacitor C46 and grounded through said capacitor C46 and a 10KΩ resistor R4. Pins 12, 16, 17, 18, 19, 13, 14 and 15 are connected to CDCLK, I2SSCLK, I2SLRCK, I2SSDI, I2SSDO, L3MODE, L3CLOCK, L3DATA, respectively. Pins 3, 7, 25 are connected with each other and then connected to AU-AVDD33V, grounded through a 10μ capacitor C71, and connected to VDD33V through an inductor 14. Pin 10 is connected with VDD33V. Such configuration is simple in structure but with reliable performances.

Preferably, the electric level shifting function of the electric level shifting and converting circuit is to convert the 1.75V-referenced ultra-low frequency DC signal from the control module 10 into a 0V-referenced AC signal. The electric level conversion function is to convert the high electric level of the mute signal output from the control module from 3.3V into 5V by using of an inverter chip with open collector. The electric level shifting and converting circuit 20 is designed such that it acts as an interface circuit between the control module 10 and the output module 30 and having following major functions.

1. Electric level shifting. The ultra-low frequency signal from the control module 10 is the 1.75V-referenced DC signal. The objective of the electric level shifting is to convert such signal into the 0V-referenced AC signal, so that the AC ultra-low frequency magnetic field can be generated after the subsequent power amplification.

2. Electric level conversion. The mute signal from the control module 10 has a high electric level of 3.3V. Such an electric level and the driving capacity are insufficient to accomplish the mute for the power amplifier. Therefore, an inverter chip 74LS06 with open collector is used in this invention to realize the electric level conversion from 3.3V to 5V, increasing thus the driving capacity.

Figure 3:
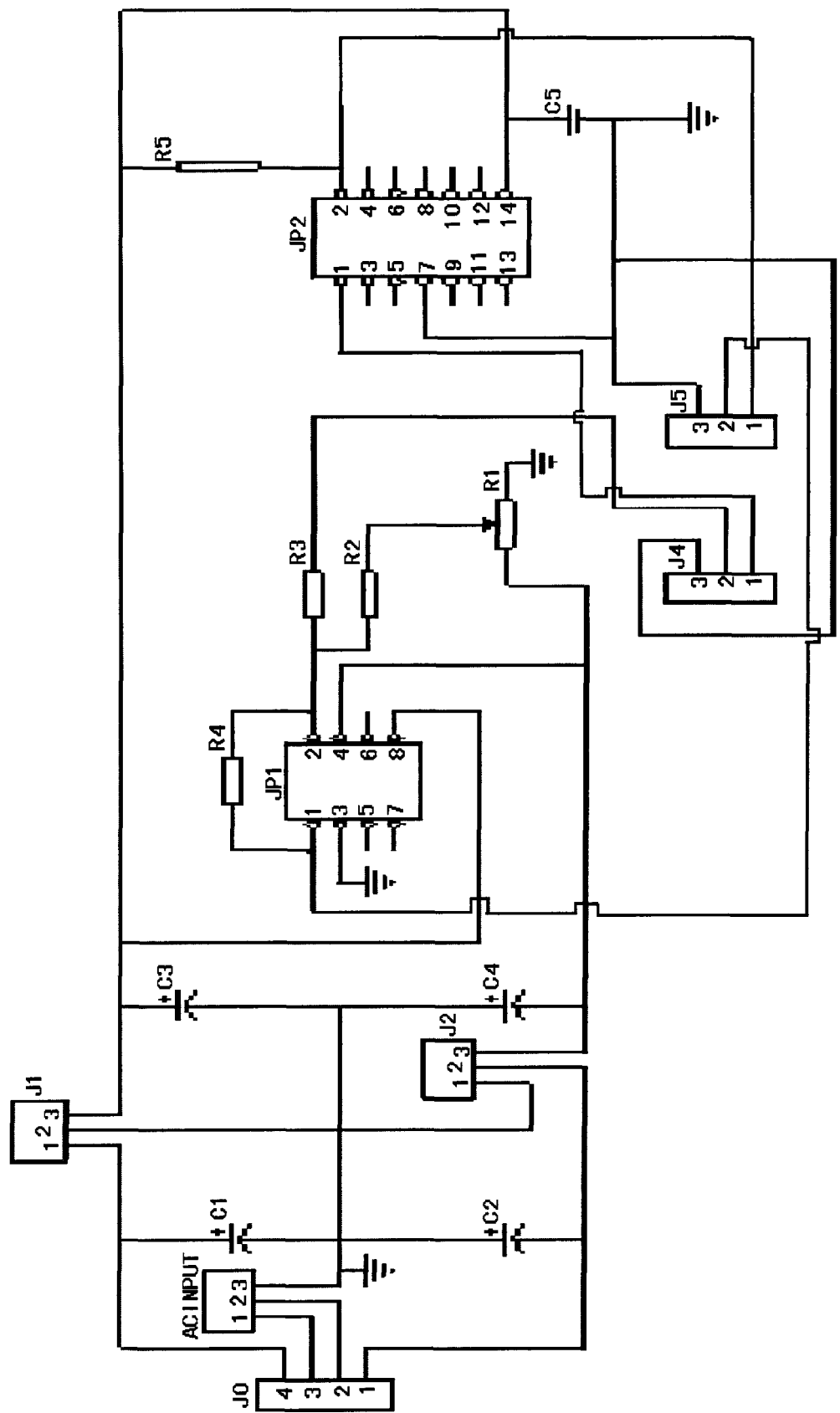
FIG. 3 shows the schematic diagram of the electric level shifting and converting circuit of the ultra-low frequency magnetic stimulating device according to the invention.

Preferably, as shown in FIG. 3, the electric level shifting and converting circuit 20 includes a rectifier bridge, a voltage regulator, electrolytic capacitors, potentiometers, resistors, a NE5532 amplifier, a 74LS06 inverter, and three external terminals for power input, signal input and signal output. Two channels of 12V AC currents from the terminals 1, 2 of the power connector ACINPUT are connected in-series and then connected to the terminals 2, 3 of the rectifying bridge J0. A plus voltage and a minus voltage generated by the rectifying bridge J0 are connected to the terminal 1 of the 7805 plus voltage regulator chip J1 and the terminal 2 of the 7905 minus voltage regulator chip J2 respectively, through its terminals 4 and 1. The minus terminal 3 of the power connector ACINPUT is grounded and connected to the terminal 2 of the 7805 plus voltage regulator chip J1 and the terminal 1 of the 7905 minus voltage regulator chip J2, and are further connected with the terminals 1 and 3 of the plus voltage regulator chip J1 and the terminals 2 and 3 of the minus voltage regulator chip J2 respectively, through a 1000 µF capacitor C1, a 1000 µF capacitor C3, a 1000 µF capacitor C2, and a 1000 µF capacitor C4. The terminal 3 of the plus voltage regulator chip J1 is connected to the terminal 8 of the NE5532 amplifier JP1. The terminal 1 of the amplifier JP1 is connected to the terminal 1 of the output connector J5. The terminal 1 and the terminal 2 of the amplifier JP1 are connected in-series through a 6KΩ resistor R4. The terminal 3 of the minus voltage regulator J2 and the terminal 4 of the amplifier JP1 are connected in-series and then grounded through an adjusting potentiometer R1. The terminal 2 of the amplifier JP1 is connected to the terminal 2 of the input connector J4 through a 6KΩ resistor R3, and is further connected to the adjusting potentiometer R1 through a 15 k resistor R2. The terminal 3 of the plus voltage regulator chip J1, the capacitor C3 and the terminal 8 of the amplifier JP1 are connected in-series, and then connected to the terminal 14 of a 74LS06 open-collector inverter JP2 and to the terminal 2 of the inverter JP2 through a 33KΩ resistor R5. The terminal 14 of the inverter JP2 is grounded through a 0.1 µF capacitor C5 that is connected to the terminal 3 of the input connector J4, the terminal 3 of the output connector J5, and the terminal 7 of the inverter JP2 before the grounding. The terminal 1 of the inverter JP2 is connected to the terminal 1 of the input connector J4. The terminal 2 of the inverter JP2 is connected to the terminal 1 of the output connector J5. The output signal LINEOUT L in FIG. 2 is connected to the terminal 2 of the input connector J4, while the output signal LINEOUT B is floated.

Thus, said circuit is composed of the rectifiers, the voltage regulators, the electrolytic capacitors, the potentiometers, the resistors, NE5532 amplifiers, 74LS06 inverters and three external connectors for power supply, signal input and signal output. The operational principle of it is that two channels of 12V AC currents from the power supply are connected in-series and fed into the rectifier to generate one channel of plus voltage and one channel of minus voltage, which are fed into the 7805 plus voltage regulator and the 7905 minus voltage regulator respectively to generate a plus 5V DC voltage and a minus 5V DC voltage as the power supply to the NE5532 amplifier. The electric level shifting is formed by an adder circuit composed of the NE5532 amplifier, resistors and potentiometers and is realized electric level shifting through adjusting the potentiometers.

1) Rectifying bridge, which can be a 3 A line bridge, being fed with two channels of 12V AC currents from two input terminals, and outputting two rectified plus and minus outputs.

2) Voltage regulator, which can be formed of two rectifiers 7805 and 7905, wherein the plus voltage from the rectifying bridge is converted into 5V DC plus voltage through the rectifier 7805 while the minus voltage is converted into 5V DC minus voltage through the rectifier 7905.

3) Electrolytic capacitors, which can be 0.1 uF/25V electrolytic capacitors at both sides of the voltage regulator and be used as by-pass capacitors for suppressing the self-oscillation in the circuit and restraining the disturbance therein.

4) Operational amplifiers, which can be formed of NE5532 operational amplifier that is a DIP8 packaged chip containing double amplifiers with JFET (Junction Field Effect Transistor) inside, having strong driving capacity and a wide operational range for voltages from ±3V to ±20V.

Figure 4:
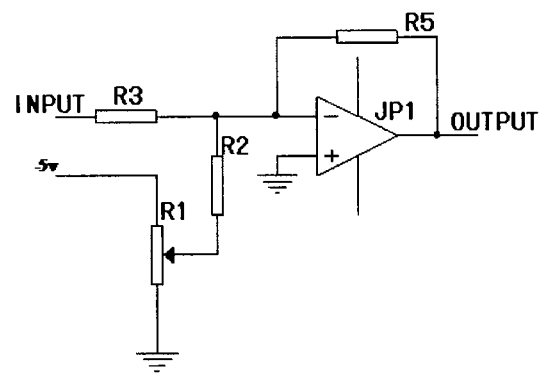
FIG. 4 shows the schematic diagram of the adder circuit of the electric level shifting and converting circuit of the ultra-low frequency magnetic stimulating device according to the invention.

The operational principle of the adder is shown in FIG. 4 with following calculation equation $$V_{out} = -\left[\frac{R_5}{R_3}V_{in} + \frac{R_5}{R_2}\left(\frac{0 \sim R_1}{R_1}\right) \times (-5)\right]$$

where $R_1$ is a 10KΩ potentiometer, $R_2$ is a 15KΩ resistor, $R_3$ and $R_5$ are respective 6KΩ resistors. Substituting these values into the above equation, it can get that the output voltage is a shifting voltage by adding 0V to −2V into the original signal.

Preferably, the audio amplifying chip of said power amplifier circuit can be of the type TDA7294. Said power amplifier circuit has a rated power output of 100 W and an operational voltage of ±32V. The output module 30 is such configured to power amplify the ultra-low stimulating signals and output the amplified signals through coils to generate AC ultra-low stimulating magnetic fields.

Figure 5:
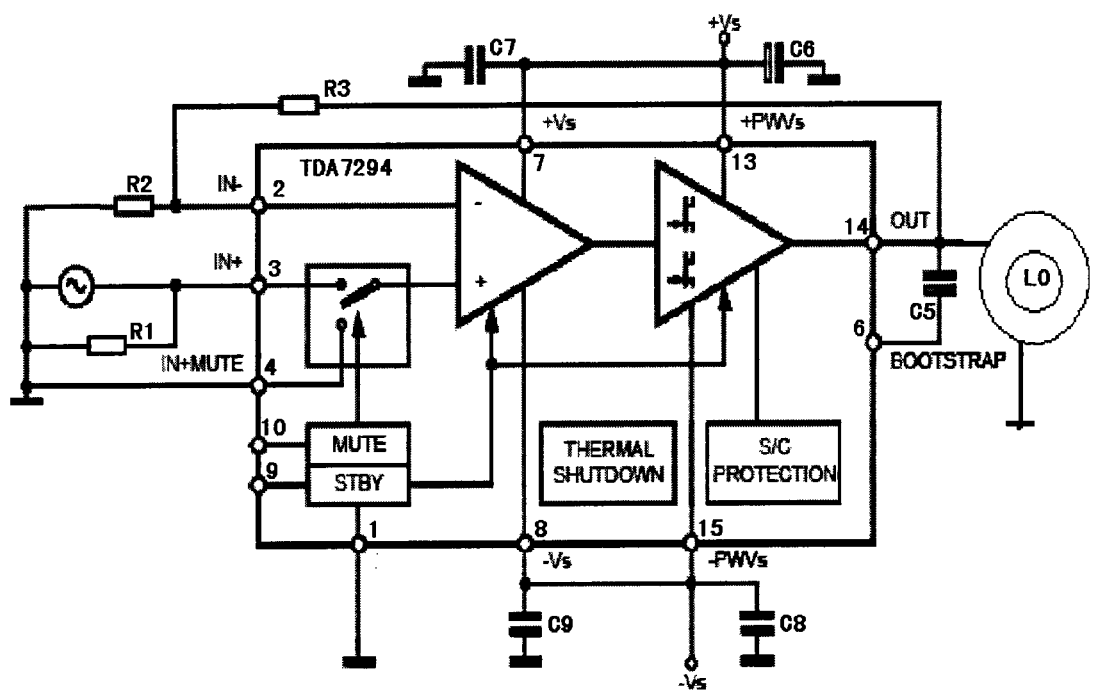
FIG. 5 shows the schematic diagram of the power-amplifying circuit of the ultra-low frequency magnetic stimulating device according to the invention.
Figure 6:
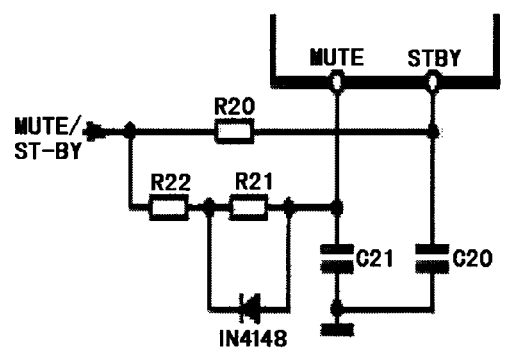
FIG. 6 shows the schematic diagram of the mute control circuit of the power-amplifying circuit of the ultra-low frequency magnetic stimulating device according to the invention.

Preferably, the power amplifier circuit is formed as shown in FIG. 5. The terminal 1 (i.e. STBY-GND) of the audio amplifier chip TDA7294 is grounded. The terminals 8 and 15 of the audio amplifier chip TDA7294 are connected in-series and then connected to ground through a 100 nF capacitor C9, to an input signal −VS, and to ground through a 1000 nF capacitor C8, respectively. The terminals 7 and 13 of the audio amplifier chip TDA7294 are connected in-series and then connected to ground through a 100 nF capacitor C7, to an input signal +VS, and to ground through a 1000 nF capacitor C6, respectively. The terminal 4 of the audio amplifier chip TDA7294 is grounded. The terminal 3 of the audio amplifier chip TDA7294 is grounded through a 22KΩ resistor R1. The terminal 2 of the audio amplifier chip TDA7294 is grounded through a 680Ω resistor R2, and is further connected to the terminal 14 of the audio amplifier chip TDA7294, a 22 µF capacitor C5 and the coil 303 through a 22KΩ resistor R3. The capacitor C5 is further connected to the terminal 6 of the audio amplifier chip TDA7294. The coil 303 is further grounded. The output signal OUTPUT1 in FIG. 3 is connected to the terminal 3 of the audio amplifier chip TDA7294 as an input, which output signal can be connected to all the four audio amplifier chips. The output signal OUTPUT2 is connected to the terminal 10 of the audio amplifier chip TDA7294, which output signal can be connect to all the four audio amplifier chips.

The power amplifier circuit is formed by using the audio amplifier chip TDA7294 with a rated power of 100 W (when the working voltages are ±32V). The functions of respective components are listed below:

| Component | Recommended value | Function | Larger than the recommended value | Smaller than the recommended value |
|---|---|---|---|---|
| R1 | 22 kΩ | Input impedance | Increasing the input impedance | Decreasing the input impedance |
| R2 | 680 Ω | Closed-loop gain up to 30 DB | Decreasing the gain | Increasing the gain |
| R3 | 22 kΩ | 30 DB | Increasing the gain | Decreasing the gain |
| R4 | 22 kΩ | STBY time | Longer STBY time | Shorter STBY time |
| R5 | 10 kΩ | MUTE time | Longer MUTE time | Shorter MUTE time |
| C3 | 10 uF | MUTE time | Longer MUTE time | Shorter MUTE time |
| C4 | 10 uF | STBY time | Longer STBY time | Shorter STBY time |
| C5 | 22 uF | Bootstrap capacitor | | Low frequency signal attenuation |
| C6, C8 | 1000 uF | Power supply filtering | | |
| C7, C9 | 0.1 uF | Power supply filtering | | |

The above electronic components can have values larger or smaller than the recommended values. In particularly, R1 is used for the input impedance, which can increase the input impedance when its value is larger than the recommended value and decrease the input impedance when its value is less than the recommended value. R2 is used for getting the closed-loop gain up to 30 DB, which can increase the gain when its value is larger than the recommended one and decrease the gain when its value is less than the recommended one. R3 is also used for getting the closed-loop gain up to 30 DB, which can increase the gain when its value is larger than the recommended one and decrease the gain when its value is less than the recommended one. R4 is used for the STBY time, which can increase the STBY time when its value is larger than the recommended one and decrease the STBY time when its value is less than the recommended one. R5 is used for the MUTE time, which can increase the MUTE time when its value is larger than the recommended one and decrease the MUTE time when its value is less than the recommended value. C3 is also used for the MUTE time, which can increase the MUTE time when its value is larger than the recommended one and decrease the MUTE time when its value is less than the recommended one. C4 is used for the STBY time, which can increase the STBY time when its value is larger than the recommended one and decrease the STBY time when its value is less than the recommended one. C5 is a bootstrap capacitor, which can attenuate the low frequency signal when its value is less than the recommended value. C6 and C8 are used for the power supply filtering. C7 and C9 are also used for the power supply filtering.

Preferably, the audio amplifier chip of said power amplifier circuit can be of a type of TDA7294, wherein said power amplifier circuit is designed to have a rated power output of 100 W and an operational voltage of ±32V, so as to get good matching in the circuit.

Preferably, the power amplifier circuit further includes a mute control circuit. As shown in FIG. 65, in the mute control circuit, the terminal STBY of the audio amplifier chip TDA7294 is connected to the terminal 4 of same chip through a 20KΩ resistor R20, and is grounded through a 10 μF capacitor C20. The terminal MUTE of the audio amplifier chip TDA7294 is grounded through a 10 μF capacitor C21, and is further connected in-series with the connecting line between the terminal 4 of the same chip and the resistor R20 through a 30KΩ resistor R21 and a diode IN4148, which are connected in parallel, and a 10KΩ resistor R22 in turn. The power amplifier circuit is configured to possess mute control function, so as to ensure a zero output and no interference current in the coils when there is no need to output the magnetic field. As shown in FIG. 5, when the terminal MUTE is at a high level (e.g. +5V), the TDA7294 chip works normally to amplify the power of the input signal. When the terminal MUTE is at low level (e.g. <2.5V), the chip TDA7294 is in mute mode, i.e., no current output whatever there is or is no input signal.

Preferably, the output from the device can be a non-pulsed ultra-low frequency current, electric field or magnetic field with the frequency lower than 0.2 Hz. The output current can be used for electrotherapy when it is output to the electrodes or for magnetotherapy when it is output to the coils. The output current can be a non-pulsed ultra-low frequency current with mono-frequency and a combination of a non-pulsed ultra-low frequency current with multi-frequency, wherein the mono-frequency current and the multi-frequency current can be output simultaneously or in a time-sharing mode. Alternatively, the output current can be a combination of the currents with multiple frequencies, which can be combined and output in a modulated mode or in a superposed mode.

Preferably, the stimulating frequency can be continuously adjusted in a step of 0.001 Hz from 0.001 Hz to 20 Hz. Corresponding frequencies can be selected through the adjustment, such as 0.001 Hz, 0.002 Hz, 0.003 Hz, 0.005 Hz, 0.01 Hz, 0.1 Hz, 0.2 Hz, 0.5 Hz, 1 Hz, 2 Hz, 4 Hz, 8 Hz, 10 Hz, 16 Hz, 18 Hz, etc. The maximum magnetic strength can be 200 Gauss, which can be adjusted continuously. The output wave can be in the form of a single sinusoidal wave or a superposition of plurality of sinusoidal waves. The device of the invention is designed to perform a magnetic induction to a human brain by using of the alternating ultra-low frequency continuous magnetic field, in order to cure or release the diseases related to human brains or mentality.

It is should be noted that the device can be powered by a transformer with a power of 1500 W, a primary input of 220 VAC, a secondary output including two channels of 28 VAC and two channels of 12 VAC, wherein two channels of 28 VAC are connected in-series and rectified for providing the power supply to the power amplifier circuit board, while two channels of 12 VAC are connected in-series and rectified for providing the power supply to the electric level shifting and converting circuit and the ARM control module.

The invention further provides an operational method of the ultra-low frequency magnetic stimulating device, including: Step 1, generating a DC stimulating signal of a frequency lower than 20 Hz; Step 2, level-shifting the stimulating signal to obtain an AC stimulating signal; and Step 3, power-amplifying the AC stimulating signal to generate a current, an electric field or a magnetic field.

INDUSTRIAL APPLICATION

The output from the ultra-low frequency magnetic stimulating device according to the invention is a non-pulsed ultra-low frequency (lower than 20 Hz) current, electric field or magnetic field. The output current can be used for electrotherapy when being output to the electrodes, or for magnetotherapy when being output to the coils. The output current is a continuous and non-pulsed ultra-low frequency current with a mono-frequency and a combination of a continuous and non-pulsed ultra-low frequency current with multi-frequency, which can be output simultaneously or in a time-sharing mode. The current with multiple frequencies can be combined and output in a modulated mode or in a superposed mode, for medical treatment. The alternating ultra-low frequency magnetic field is used here to perform magnetic induction to human brains, in order to cure or release the diseases related to human brains or mentality.

What is claimed is:

1. An ultra-low frequency magnetic stimulating device for curing and remitting disease related to the brain, comprising:
   a control module including a processor and an audio chip, wherein said audio chip generates a stimulating signal with a stimulating frequency of higher than 0.001 Hz and lower than 0.1 Hz under control of the processor;
   an electric level shifting and converting circuit, for shifting an electric level of said stimulating signal to form an AC stimulating signal; and
   an output module including at least one power amplifying circuit, whose output terminal is connected with a coil, wherein the output module power-amplifies the AC stimulating signal, generates a non-pulsed continuous ultra-low frequency magnetic field having a varying frequency of higher than 0.001 Hz and lower than 0.1 Hz, and applies the non-pulsed continuous ultra-low frequency magnetic field to the brain.

2. The ultra-low frequency magnetic stimulating device according to claim 1, further comprising a man-machine interface coupled to and communicating with the processor to achieve a man-machine interface control.

3. The ultra-low frequency magnetic stimulating device according to claim 1, wherein:
   the control module further includes a circuit board, and
   the audio chip is short-circuited through a first capacitor and a second capacitor at output terminals of the audio chip, and is grounded through a first resistor and a second resistor at the output terminals of the audio chip.

4. The ultra-low frequency magnetic stimulating device according to claim 1, wherein said AC stimulating signal takes 0V as a reference.

5. The ultra-low frequency magnetic stimulating device according to claim 1, wherein:
   said at least one power amplifying circuit includes an outputting chip, and
   the control module is further used for generating a mute control signal for the outputting chip.

6. The ultra-low frequency magnetic stimulating device according to claim 5, wherein the electric level shifting and converting circuit is further used for converting a high level of the mute control signal from 3.3V to 5V and outputting the mute control signal having the high level of 5V to the outputting chip.

7. The ultra-low frequency magnetic stimulating device according to claim 1, wherein an output current of the device includes one of a non-pulsed ultra-low frequency current with a mono-frequency, a first combination of non-pulsed ultra-low frequency current with multiple frequencies output simultaneously, or a second combination of non-pulsed ultra-low frequency current with multiple frequencies output in a time-sharing manner.

8. The ultra-low frequency magnetic stimulating device according to claim 7, wherein the current with multiple frequencies is output in a modulated mode or in a superposed mode.

9. The ultra-low frequency magnetic stimulating device according to claim 1, wherein the non-pulsed continuous ultra-low frequency magnetic field includes a combination of multiple waves having multiple frequencies and output simultaneously.

10. An operational method for an ultra-low frequency magnetic stimulating device for curing and remitting disease related to the brain, comprising:
    generating, using an audio chip under control of a processor, a stimulating signal with a stimulating frequency of higher than 0.001 Hz and lower than 0.1 Hz;
    shifting, using an electric level shifting and converting circuit, a level of said stimulating signal to form an AC stimulating signal;
    power-amplifying, using an output module including at least one power amplifying circuit whose output terminal is connected with a coil, the AC stimulating signal and generating a non-pulsed continuous ultra-low frequency magnetic field having a varying frequency of higher than 0.001 Hz and lower than 0.1 Hz; and
    applying, using the output module, the non-pulsed continuous ultra-low frequency magnetic field to the brain.

* * * * *